(12) United States Patent
Freilich

(10) Patent No.: US 10,172,740 B2
(45) Date of Patent: Jan. 8, 2019

(54) LACRIMAL STENT

(71) Applicant: David E Freilich, Englewood, NJ (US)

(72) Inventor: David E Freilich, Englewood, NJ (US)

( * ) Notice: Subject to any disclaimer, the term of this patent is extended or adjusted under 35 U.S.C. 154(b) by 564 days.

(21) Appl. No.: 14/935,101

(22) Filed: Nov. 6, 2015

(65) Prior Publication Data

US 2017/0128266 A1 May 11, 2017

(51) Int. Cl.
*A61F 2/00* (2006.01)
*A61F 9/007* (2006.01)

(52) U.S. Cl.
CPC .. *A61F 9/00772* (2013.01); *A61F 2220/0025* (2013.01); *A61F 2250/0068* (2013.01)

(58) Field of Classification Search
CPC ............ A61F 2220/0025; A61F 9/00772
See application file for complete search history.

(56) References Cited

U.S. PATENT DOCUMENTS

| 3,181,895 | A | * | 5/1965 | Cator | ............ | F16L 37/004 |
|---|---|---|---|---|---|---|
| | | | | | | 285/1 |
| 3,618,604 | A | | 11/1971 | Ness | | |
| 4,790,809 | A | | 12/1988 | Kuntz | | |
| 5,169,386 | A | | 12/1992 | Becker et al. | | |
| 5,318,513 | A | * | 6/1994 | Leib | ............ | A61F 9/00772 |
| | | | | | | 604/8 |
| 5,385,541 | A | | 1/1995 | Kirsch et al. | | |
| 5,417,651 | A | | 5/1995 | Guena et al. | | |
| 5,423,777 | A | | 6/1995 | Tajiri et al. | | |
| 5,437,625 | A | * | 8/1995 | Kurihashi | ...... | A61F 9/00772 |
| | | | | | | 128/898 |
| 5,830,171 | A | | 11/1998 | Wallace | | |
| 5,993,407 | A | | 11/1999 | Moazed | | |
| 6,016,806 | A | | 1/2000 | Webb | | |
| 6,041,785 | A | | 3/2000 | Webb | | |
| 6,196,993 | B1 | | 3/2001 | Cohan et al. | | |
| 6,375,972 | B1 | | 4/2002 | Guo et al. | | |
| 6,527,780 | B1 | | 3/2003 | Wallace et al. | | |
| 6,605,108 | B2 | | 8/2003 | Mendius et al. | | |

(Continued)

FOREIGN PATENT DOCUMENTS

| WO | 09965544 | 12/1999 |
|---|---|---|
| WO | 2011005955 A2 | 1/2011 |
| WO | 2015002510 A1 | 1/2015 |

OTHER PUBLICATIONS

International Search Report and Written Opinion, PCT /US2016/059997, dated Feb. 1, 2017, 8 pages.

*Primary Examiner* — Leslie Deak
(74) *Attorney, Agent, or Firm* — Edell, Shapiro & Finnan, LLC

(57) ABSTRACT

Provided herein is a lacrimal stent that includes a flexible tube. The flexible tube includes a first distal end, a second distal end, and an elongated body between the first distal end and the second distal end. A first magnet is arranged at the first distal end of the flexible tube, and a magnetic material is arranged at the second distal end of the flexible tube. When the first distal end of the flexible tube is inserted into a lacrimal sac of an eye through a first punctum and the second distal end is inserted into the lacrimal sac of the eye through a second punctum, a magnetic attraction between the first magnet and the magnetic material causes the flexible tube to flex so that the first magnet of the first distal end magnetically engages the magnetic material of the second distal end.

20 Claims, 10 Drawing Sheets

(56) References Cited

U.S. PATENT DOCUMENTS

| | | |
|---|---|---|
| 7,117,870 B2 | 10/2006 | Prescott |
| 2005/0119737 A1 | 6/2005 | Bene et al. |
| 2006/0167437 A1 | 7/2006 | Valencia |
| 2008/0086101 A1 | 4/2008 | Freilich |
| 2008/0154351 A1 | 6/2008 | Leewood et al. |
| 2011/0257724 A1 | 10/2011 | Kantor |
| 2012/0116504 A1 | 5/2012 | Lyons et al. |

\* cited by examiner

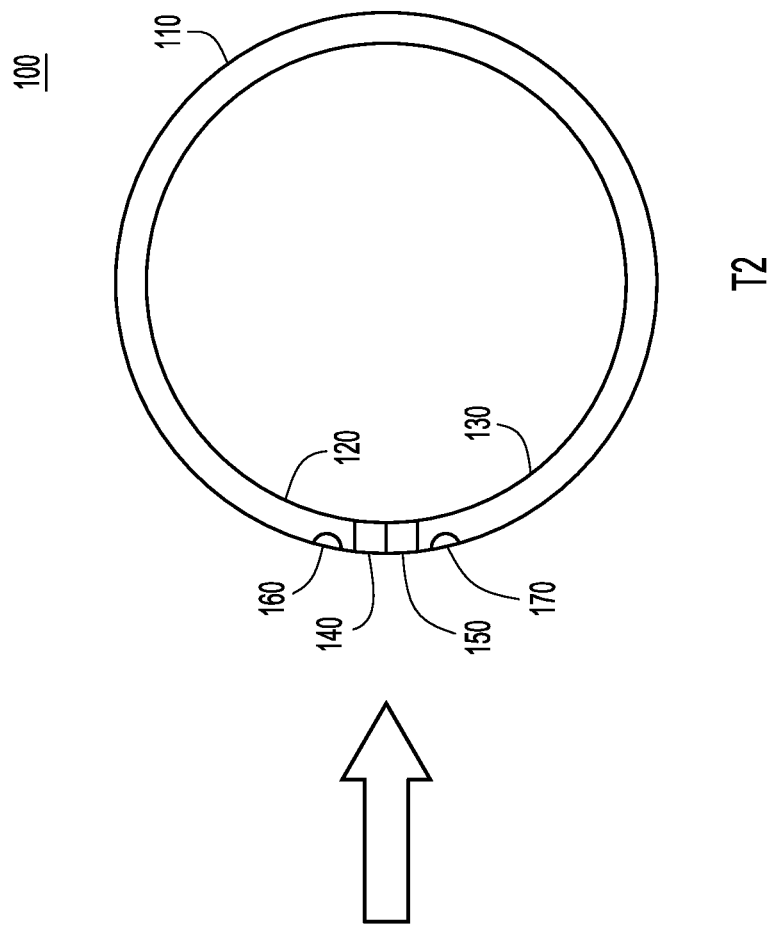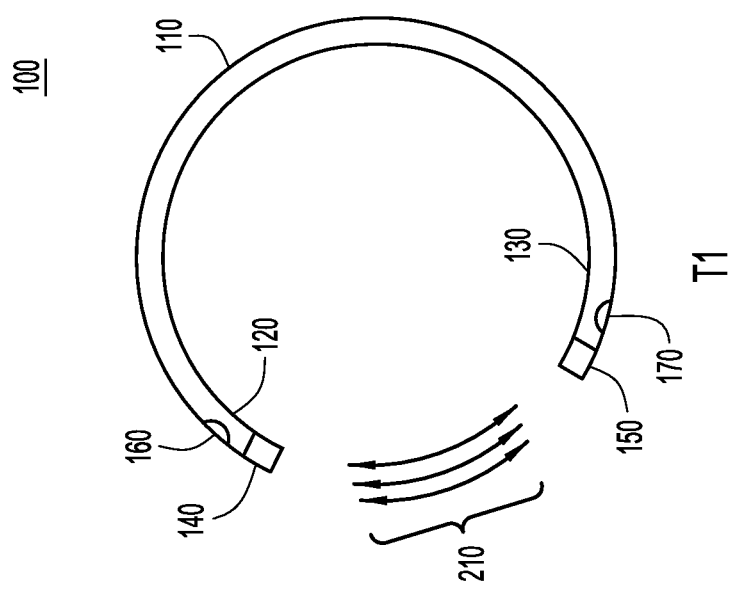
FIG.2

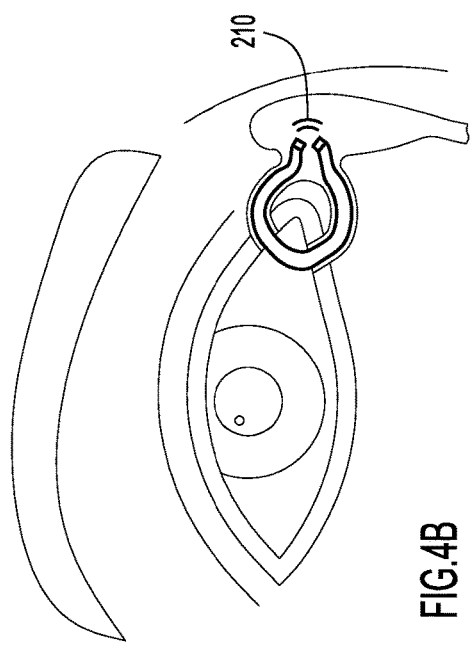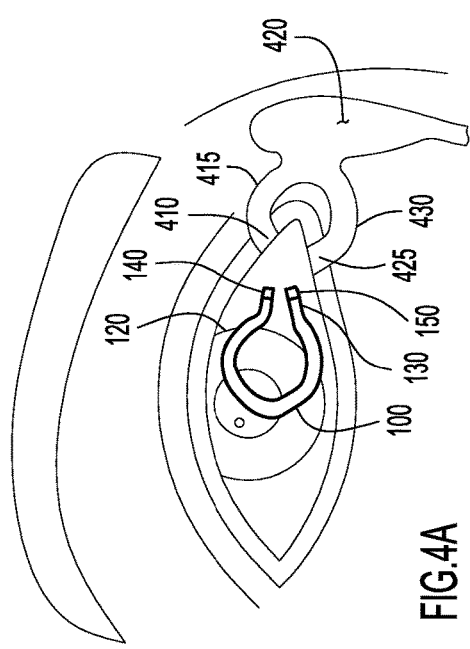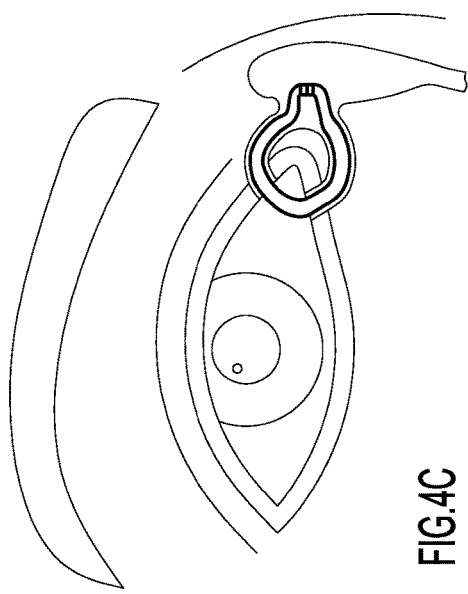

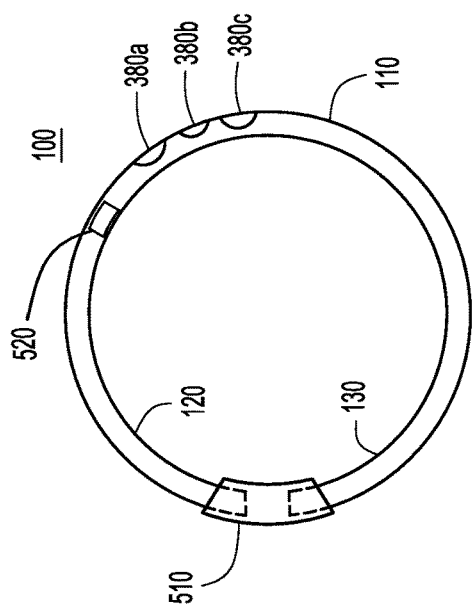
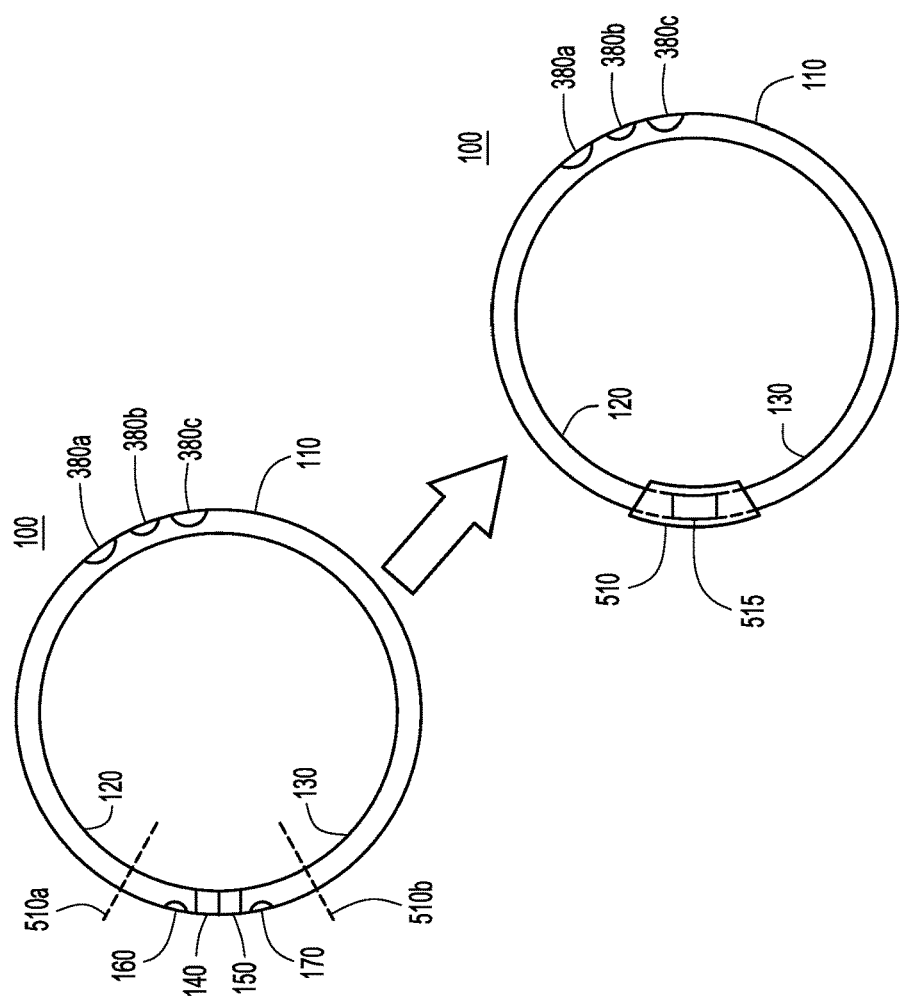
FIG.5A
FIG.5B

800

810 — INSERTING A FLEXIBLE TUBE INTO A LACRIMAL SAC OF AN EYE, WHEREIN THE FLEXIBLE TUBE COMPRISES A FIRST DISTAL END, A SECOND DISTAL END, AN ELONGATED BODY BETWEEN THE FIRST DISTAL END AND THE SECOND DISTAL END, A FIRST MAGNET ARRANGED AT THE FIRST DISTAL END OF THE FLEXIBLE TUBE, AND A MAGNETIC MATERIAL ARRANGED AT THE SECOND DISTAL END OF THE FLEXIBLE TUBE, WHEREIN INSERTING THE FLEXIBLE TUBE INTO THE LACRIMAL COMPRISES INSERTING THE FIRST DISTAL END OF THE FLEXIBLE TUBE INTO A FIRST PUNCTUM AND INSERTING THE SECOND DISTAL END INTO A SECOND PUNCTUM

820 — ONCE INSERTED, THE FLEXIBLE TUBE FLEXES IN RESPONSE TO A MAGNETIC ATTRACTION BETWEEN FIRST MAGNET OF THE FIRST DISTAL END AND THE MAGNETIC MATERIAL OF THE SECOND DISTAL END SUCH THAT THE FIRST MAGNET MAGNETICALLY ENGAGES THE MAGNETIC MATERIAL

FIG.8

LACRIMAL STENT

TECHNICAL FIELD

The present disclosure relates to stents, and in particular, lacrimal stents.

BACKGROUND

Lacrimal bicanalicular stents may be used to stent the punctum and canaliculus for conditions that cause punctal and canalicular stenosis.

Many ophthalmic and systemic conditions can cause stenosis and closure of the punctum and canaliculus, causing patients to have chronic tearing which can cause irritation and decreased visual acuity. These conditions can include congenital conditions, infection, inflammation, chemotherapy and trauma. Current treatments for stenosis and closure of the punctum and canaliculus involve stenting the nasal lacrimal duct system with either a bicanaliculus stent that goes down into the nose or a self retaining bicanalicular stent that sits in the nasal lacrimal sac. A third possibility is a monocanalicular stent that either sits in the upper or lower punctum and canaliculus and goes into the nasal lacrimal sac or into the nasal cavity. Each of these stents has specific disadvantages.

Current bicanalicular stents have to be placed in an operating room with the patient under anesthesia. This type of stent has to be passed into the nose and retrieved out of the nose. It can be very difficult to locate and retrieve the stent out of the nasal cavity. The process of placing such a stent can have complications such as nose bleeds and complications due to anesthesia. Also, anchoring the stents so they do not dislodge is complicated, and often the stents will dislodge.

Monocanalicular stents may be placed under local anesthesia, but it is very hard to determine where the distal end of the stent sits within the lacrimal system. The stent, which has a collarette, also sits in the punctum and occludes tears from draining into the lacrimal system, which causes constant tearing while the stent is in place. These stents also have a tendency to be dislodged. Furthermore, monocanalicular stents only treat one of the nasal lacrimal drainage systems, either the upper or lower system, but not both.

The vast majority of eye medication is delivered via liquid drops by a conventional eye dropper. While this delivery mechanism has proven effective, it also has several drawbacks. For example, much of the medication runs off the eye before it can be absorbed or penetrate into the eye. Further, the medication is not applied uniformly over time in that there is an initial higher concentration of drug immediately upon application, as compared to subsequent time periods. Finally, patients often forget to use their medication, or are incapable of properly administering the drops for themselves. In other words, it is not uncommon for patients to fail to medicate themselves sufficiently, or at the correct times.

BRIEF DESCRIPTION OF THE DRAWINGS

FIG. 2 is an illustration of magnetic engagement of a first distal end and a second distal end of a lacrimal stent, according to an example embodiment.

FIGS. 4A-E illustrate a process for placing a lacrimal stent, according to an example embodiment.

FIG. 5A illustrates a first process for securing a first distal end and a second distal end of a lacrimal stent within a sleeve, according to an example embodiment.

FIG. 5B illustrates a second process for securing a first distal end and a second distal end of a lacrimal stent within a sleeve, according to an example embodiment.

FIG. 8 is a flowchart illustrating a process for placing a lacrimal stent, according to an example embodiment.

DESCRIPTION OF EXAMPLE EMBODIMENTS

Overview

Provided herein is a lacrimal stent that includes a flexible tube. The flexible tube includes a first distal end, a second distal end, and an elongated body between the first distal end and the second distal end. A first magnet is arranged at the first distal end of the flexible tube, and a magnetic material is arranged at the second distal end of the flexible tube. When the first distal end of the flexible tube is inserted into a lacrimal sac of an eye through a first punctum and the second distal end is inserted into the lacrimal sac of the eye through a second punctum, a magnetic attraction between the first magnet and the magnetic material causes the flexible tube to flex so that the first magnet of the first distal end magnetically engages the magnetic material of the second distal end.

EXAMPLE EMBODIMENTS

Figure 1:
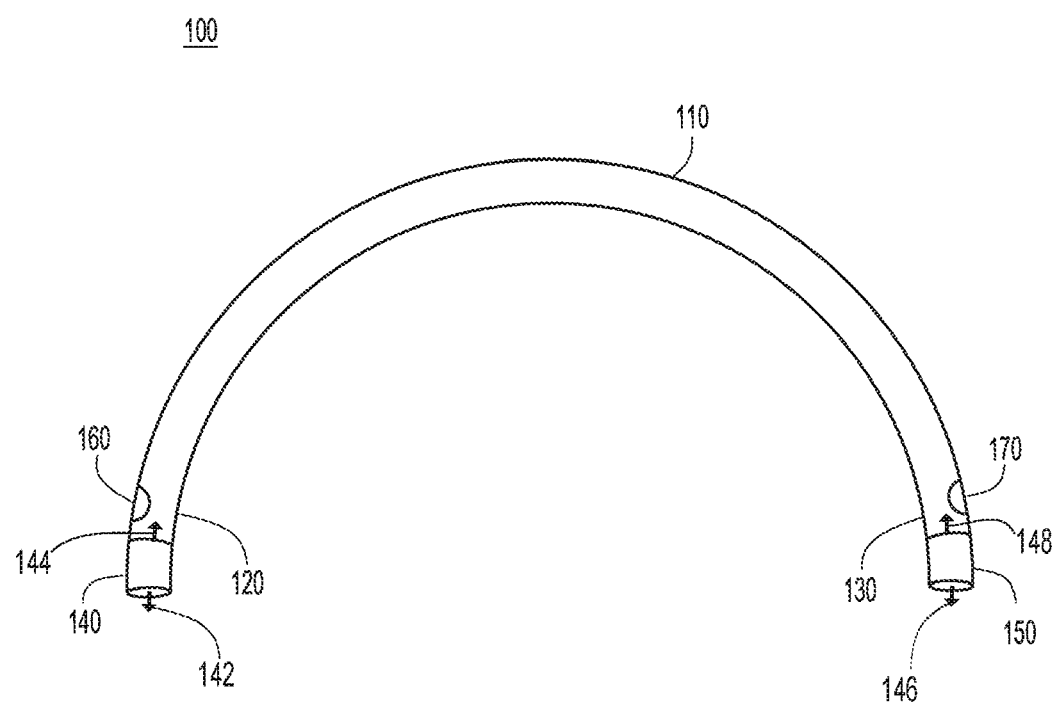
FIG. 1 is a first example lacrimal stent, according to an example embodiment.

With reference now made to FIG. 1, depicted therein is a lacrimal bicanalicular stent 100. Stent 100 comprises a flexible elongated body 110 with a first distal end 120 and a second distal end 130. Flexible elongated body may be constructed from a flexible material, such as silicone, to form a flexible tube. Included on first distal end 120 is a magnet 140. Included on second distal end 130 is a magnetic material 150. In some example embodiments, magnetic material 150 is a second magnet, while in other example embodiments, magnetic material 150 is a magnetic material that will be magnetically attracted to magnet 140, but is itself not a magnet. For example, magnetic material 150 may be a ferrous material that reacts to a magnetic field, while not itself being a magnet. Also included in stent 100 are a first one-way valve 160 on the first distal end 120, and a second one-way valve 170 on the second distal end 130. The use of first one-way valve 160 and second one-way valve 170 will be described later with reference to FIG. 9.

Through the use of magnet 140 and magnetic material 150, first distal end 120 and second distal end 150 may be brought into contact as illustrated in FIG. 2. As shown in FIG. 2, at time T1, first distal end 120 is brought sufficiently close to second distal end 130, causing magnetic force 210 to form between first magnet 140 and magnetic material 150. Specifically, magnetic force 210 is sufficiently strong such that magnetic force 210 flexes the flexible material of elongated body 110, bringing first distal end 120 into magnetic engagement with second distal end 130 at time T2.

According to some example embodiments, magnetic material 150 may be a second magnet similar to first magnet 140. In such an embodiment, the poles of first magnet 140 and second magnet 150 may both be axially aligned with elongated body 110. For example, a north pole 142 of first magnet 140 may be arranged at the distal face of first magnet 140 and axially aligned with elongated body 110, and a south pole 144 of the first magnet may be arranged at the proximal face of first magnet 140 and axially aligned with elongated body 110. A south pole 146 of second magnet 150 may be arranged at the distal face of second magnet 150 and axially aligned with elongated body 110, and a north pole 148 of the second magnet may be arranged at the proximal face of second magnet 140 and axially aligned with elongated body 110. Because the north pole 142 of first magnet 140 will be attracted to the south pole 146 of second magnet 150, such an arrangement may ensure that the distal face of first magnet 140 magnetically engages the distal face of second magnet 150 when first magnet 140 and second magnet 150 are brought into magnetic engagement at time T2.

Figure 3:
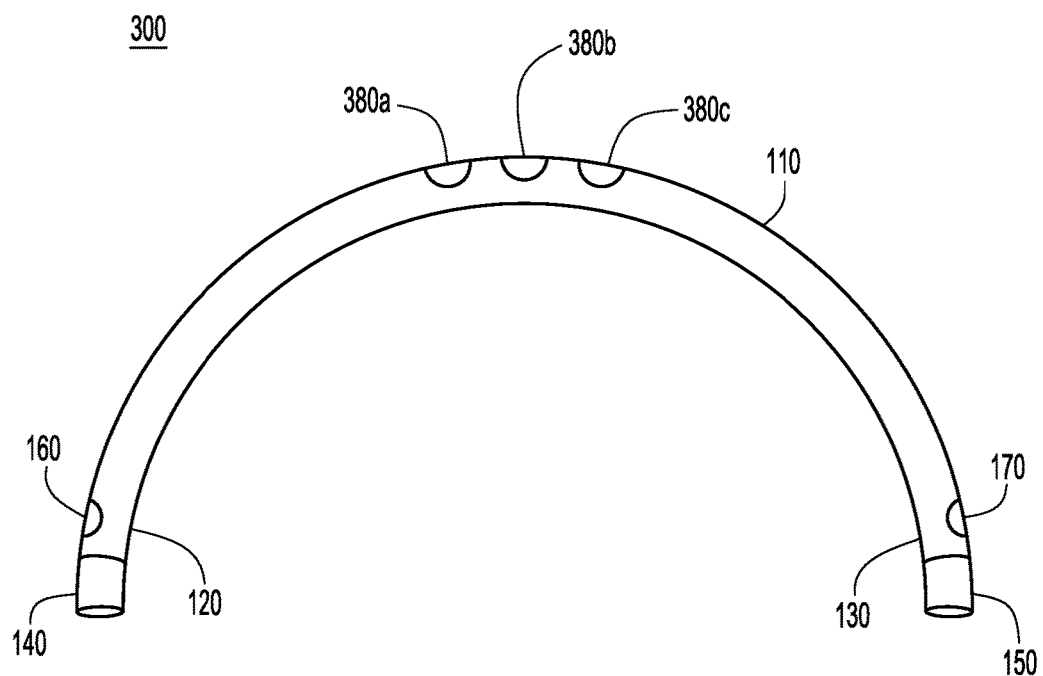
FIG. 3 is a medication releasing lacrimal stent, according to an example embodiment.

With reference now made to FIG. 3, depicted therein is another example embodiment, illustrating stent 300. Stent 300 is similar to stent 100 of FIGS. 1 and 2, and therefore, like reference numerals have been used to reference similar parts. Stent 300 of FIG. 3 differs from stent 100 of FIGS. 1 and 2 through the inclusion of openings 380a-c. Openings 380a-c may be used to provide medicine or other materials to the surface of the eye, as will be explained below with reference to FIG. 7. Specifically, one or more of openings 380a-c may be used to provide sustained release of medicine to the surface of an eye.

With reference now made to FIGS. 4A-4E, depicted therein is a process for placing a stent, like stent 100 of FIGS. 1 and 2 or stent 300 of FIG. 3. Illustrated in 4A are superior punctum 410 which leads through superior canaliculus 415 to lacrimal sac 420. Similarly, inferior punctum 425 leads through inferior canaliculus 430 to lacrimal sac 420.

As illustrated in FIG. 4B, first distal end 120, including first magnet 140, is inserted through superior punctum 410, through superior canaliculus 415, into lacrimal sac 420. Similarly, second distal end 130, including magnetic material 150, is inserted through inferior punctum 425, through inferior canaliculus 430, into lacrimal sac 420. The insertion of the first distal end 120 and the second distal end 130 into the lacrimal sac 420 may be accomplished through the use of one or more insertion tools, as will be described below with reference to FIG. 9.

Once arranged in lacrimal sac 420, magnetic force 210 between first magnet 140 and magnetic material 150 will cause first magnet 140 to come into magnetic engagement with magnetic material 150, as illustrated in FIG. 4C.

Figure 4E:
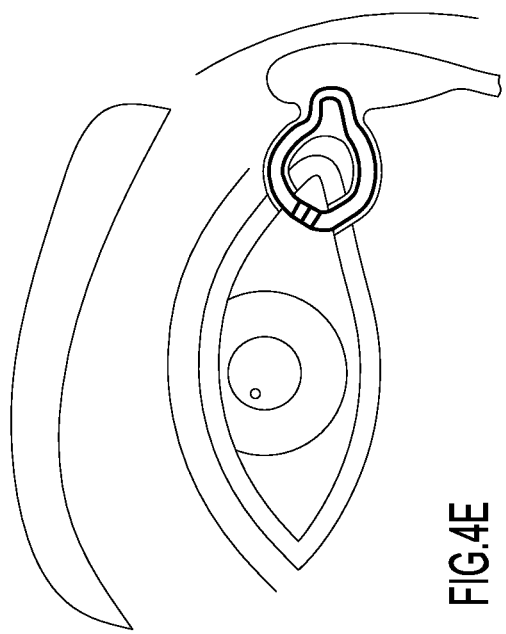
Figure 4D:
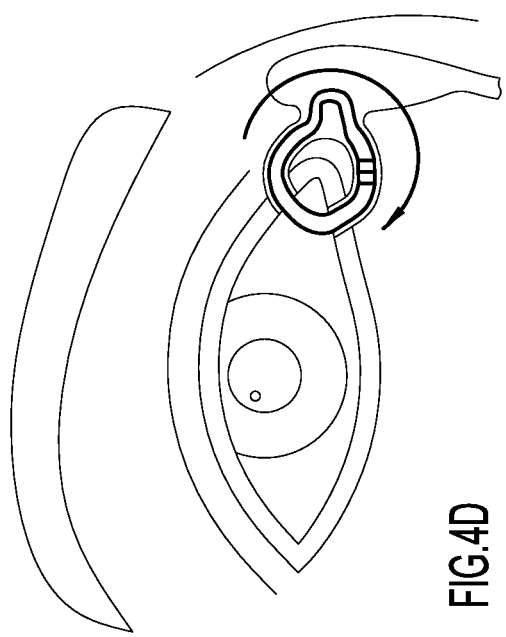

Once the first magnet 140 and the magnetic material 150 are magnetically engaged, the entire stent 100 can be rotated as illustrated in FIG. 4D. As illustrated in the FIG. 4D, stent 100 may be rotated clockwise so that, for a left eye, the first magnet 140 and magnetic material 150 traverse the inferior canaliculus 430. The techniques described herein also permit first magnet 140 and magnetic material 150 to traverse superior canaliculus 415.

As illustrated in FIG. 4E, the rotation continues until first distal end 120, including first magnet 140, and second distal end 130, including magnetic material 150, exit inferior canaliculus 430 through inferior punctum 425 (or superior canaliculus 415 through superior punctum 410). Once first distal end 120 (including first magnet 140) and second distal end 130 (including magnetic material 150) are accessible, stent 100 can be prepared to serve as either an intubating and/or medication releasing stent.

As illustrated in FIG. 5A, first distal end 120 may be trimmed through cut 510a and second distal end 130 may be trimmed through 510b. First distal end 120 and second distal end 130 are trimmed to remove first magnet 140 and magnetic material 150. While cuts 510a and 510b also show the trimming of one-way valves 160 and 170, the trimming of first distal 120 and second distal end 130 may be made such that one-way valves 160 and 170 remain on stent 100.

Once trimmed, first distal end 120 and second distal end 130 may be anchored in sleeve 510. When stent 100 is to serve as a medicine release stent, medical reservoir 515 may be included in sleeve 510. First distal end 120 and second distal end 130 may fit into openings in reservoir 515, allowing medication to flow through elongated body 110. First distal end 120 and second distal end 130 may be secured in sleeve 510 with or without sutures.

According to another example embodiment illustrated in FIG. 5B, medical reservoir 520 may be arranged directly within elongated body 110, and not within sleeve 510. The medicine within reservoir 520 may flow to the eye through openings 380a-c. A stent like that of the example embodiment of FIG. 5B may provide benefits over medicine delivering punctal plugs, as stent 100 of FIG. 5B delivers medicine to an eye while still allowing tears to drain around stent 100.

Figure 6A:
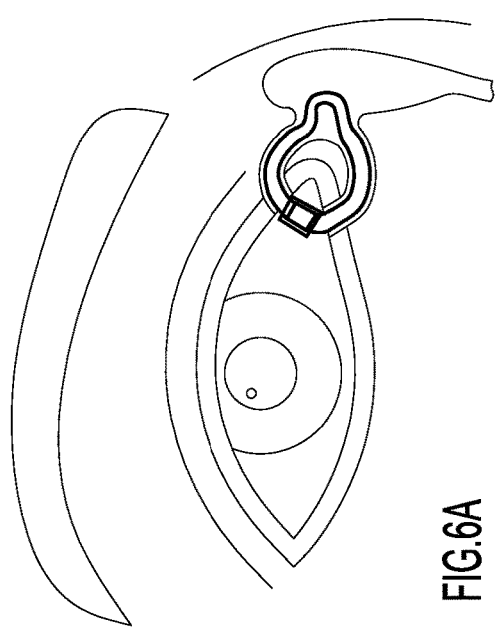
FIGS. 6A-C illustrate a further process for placing a lacrimal stent, according to an example embodiment.
Figure 6B:
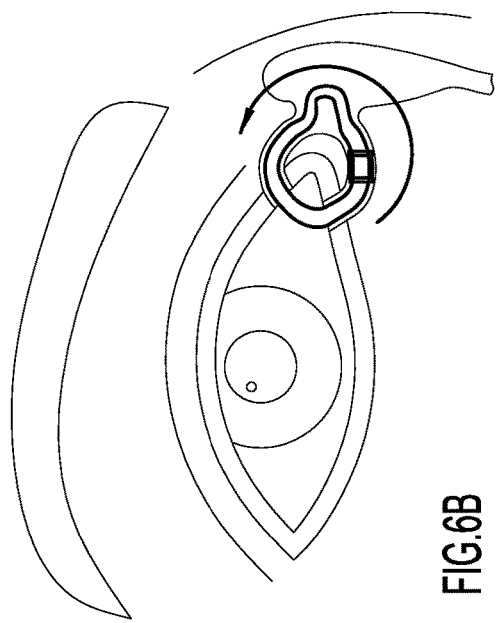
Figure 6C:
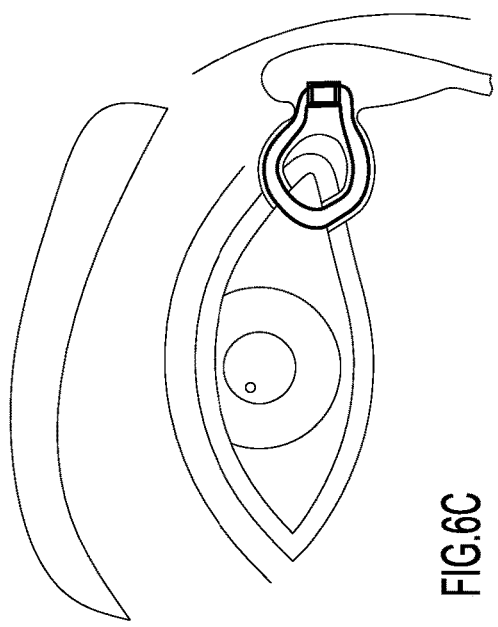

The process of placing stent 100 continues with reference to FIGS. 6A-C. As illustrated in FIG. 6A, stent 100 (including sleeve 510) may be rotated so that sleeve 510 becomes arranged within lacrimal sac 420. As illustrated in FIG. 6B, the rotation of stent 100 causes first distal end 120 and second distal end 130 (including sleeve 510) to enter either superior punctum 410 or inferior punctum 425. First distal end 120 and second distal end 130 (including sleeve 510) traverse either of superior canaliculus 415 or inferior canaliculus 430 until sleeve 510 becomes arranged within lacrimal sac 420. Once placed, stent 100 may serve as either an intubation stent or as a medication releasing stent. When serving as a medication releasing stent, openings 380a-c facilitate the release of medication contained in medical reservoir 515 (or a medical reservoir such as reservoir 520 of FIG. 5B).

Through the use of sleeve 510 and medical-reservoir 515 (or a medical reservoir such as reservoir 520 of FIG. 5B), stent 100 may be used to treat many different ophthalmic conditions which affect both the anterior and posterior segments of the eye. These ophthalmic conditions include both anterior and posterior diseases of the eye, such as dry eye, allergic conditions, lid margin diseases, corneal diseases, infectious conditions of the anterior segment, cornea and posterior segment (e.g., bacterial, viral fungal, parasitic and other conditions), inflammatory conditions of the anterior segment, cornea and posterior segment, corneal angiogenesis, retinal diseases such as age related macular degeneration, diabetic retinopathy, neurodegenerative diseases, macular edema caused by multiple etiologies, and other retinopathies including those of vascular origin.

Many different medicines may be placed in medical reservoir 515 (or a medical reservoir such as reservoir 520 of FIG. 5B) of sleeve 510 in order to treat ophthalmic conditions. These medications include anti-infective agents (e.g., antibiotics, antivirals, antifungals, antiparasitics, etc.), anti-inflammatory agents (both steroid and non-steroidal medicines), anti-allergic medications, glaucoma medications, anti-vascular endothelial growth factor (anti-VEGF)

medications, dry eye medications and lubricants, and anti-angiogenic agents, among others.

The advantages of the stent 100 releasing the medications as opposed to, for example, eye drops include sustained release of the medication over time and ensuring that the medication is being delivered to the eye. Eye drops may be difficult to apply to the eye, particularly for elderly patients. By continually releasing medication through stent 100, improved treatments and outcomes for patients may be achieved. A stent as described herein is also advantageous for the treatment of dry eye syndrome. Specifically, a stent as described herein provides constant release of lubrication onto the eye surface as opposed to the placement of intermittent drops. Furthermore, the use of a stent as described herein to provide a constant release of anti-infective agents is advantageous for the treatment of infectious diseases of the eye because the constant release of anti infective agents onto the eye surface allows for better penetration and higher concentration of the agents which results in a better treatment of the infectious disease.

As an alternative to the example embodiments of FIGS. 1-5, first magnet 140 and magnetic material 150 may be constructed having an annular shape. Accordingly, fluid may pass through the holes at the center of annular first magnet 140 and annular magnetic material 150, allowing fluid flow through the entirety of elongated body 110. When using an annular shape for first magnet 140 and magnetic material 150, it may be advantageous that magnetic material 150 comprise a second magnet to ensure proper alignment with first magnet 140, and to increase the magnetic force that keeps first magnet 140 magnetically engaged with second magnet 150. Furthermore, when using annular magnets in an intubating stent, medicine may be included in elongated body 110, sleeve 510 may be omitted, and the placement of the stent may be completed at the step illustrated in FIG. 4C.

Figure 7:
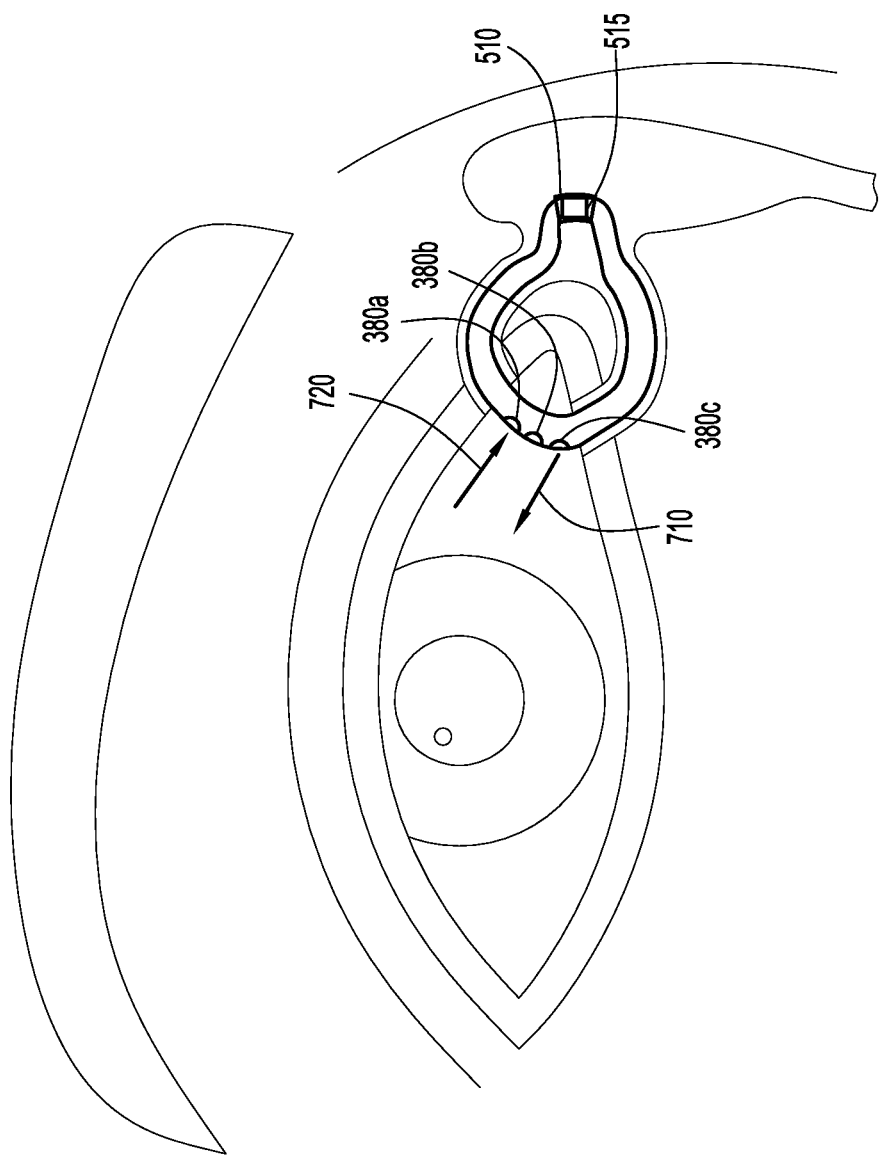
FIG. 7 illustrates the release of medicine from a medication releasing lacrimal stent, according to an example embodiment.

As illustrated in FIG. 7, medicine 710 from medical reservoir 515 (or a medicine filled reservoir such as reservoir 520 of FIG. 5B)) exits openings 380a-c, while tears 720 enter openings 380a-c. The entry of tears 720 and exit of medicine 710 forms a cycle that allows medicine 710 to be continuously released onto the surface of the eye. One or more of openings 380 may be constructed as one-way valves. Specifically, a subset of the one-way valves 380a-c may allow fluid flow into stent 100 while preventing outward flow. Another subset of one-way valves 380a-c may allow fluid flow out of stent 100 while preventing inward flow. By combining these subsets of one-way valves as well as the natural blink mechanism of the eye, a cycle may be established that continually releases medicine 710 onto the surface of the eye. Once the medicine in reservoir 515 (or reservoir 520 of FIG. 5B) is used up, stent 100 may be removed and a new stent may be placed. Stent 100 may also be rotated so that sleeve 510 is visible and removed so that a new sleeve with a new medical reservoir 515 may be placed using the same stent 100 through the process illustrated in FIG. 5A. Similarly, a new reservoir like that of reservoir 520 of FIG. 5B may be placed within elongated body 110 of stent 100. The stent 100 may then be rotated back as illustrated in FIGS. 6A-C With reference now made to FIG. 8, depicted therein is a flowchart 800 illustrating a process for placing a stent, such as stent 100 of FIGS. 1-7. The process of flowchart 800 begins in operation 810 where a flexible tube is inserted into a lacrimal sac of an eye. The flexible tube comprises a first distal end, a second distal end, an elongated body between the first distal end and the second distal end, a first magnet arranged at the first distal end of the flexible tube, and a magnetic material arranged at the second distal end of the flexible tube. In other words, the flexible tube comprises a structure like that of stent 100 of FIGS. 1-7. Inserting the flexible tube into the lacrimal sac is accomplished by inserting the first distal end of the flexible tube into a first punctum and inserting the second distal end into a second punctum. In other words, the insertion of the flexible tube follows the process illustrated through FIGS. 4A and 4B.

In operation 820, once the flexible tube is inserted, the tube flexes such that the first magnet of the first distal end magnetically engages the magnetic material of the second distal end. In other words, once both of the first distal end and the second distal end are inserted into the lacrimal sac of the eye, the magnetic field created by the first magnet cause an attraction with the magnetic material, thereby flexing the flexible tube and magnetically engaging the first magnet with the magnetic material. Accordingly, operation 820 includes the magnetic engagement of first magnet 140 with magnetic material 150 as illustrated in FIG. 4C. The process of flowchart 800 may continue to include the operations illustrated in FIGS. 4D-E, 5, 6A-C, and 7, depending on the structure and medical use of the stent.

Figure 9:
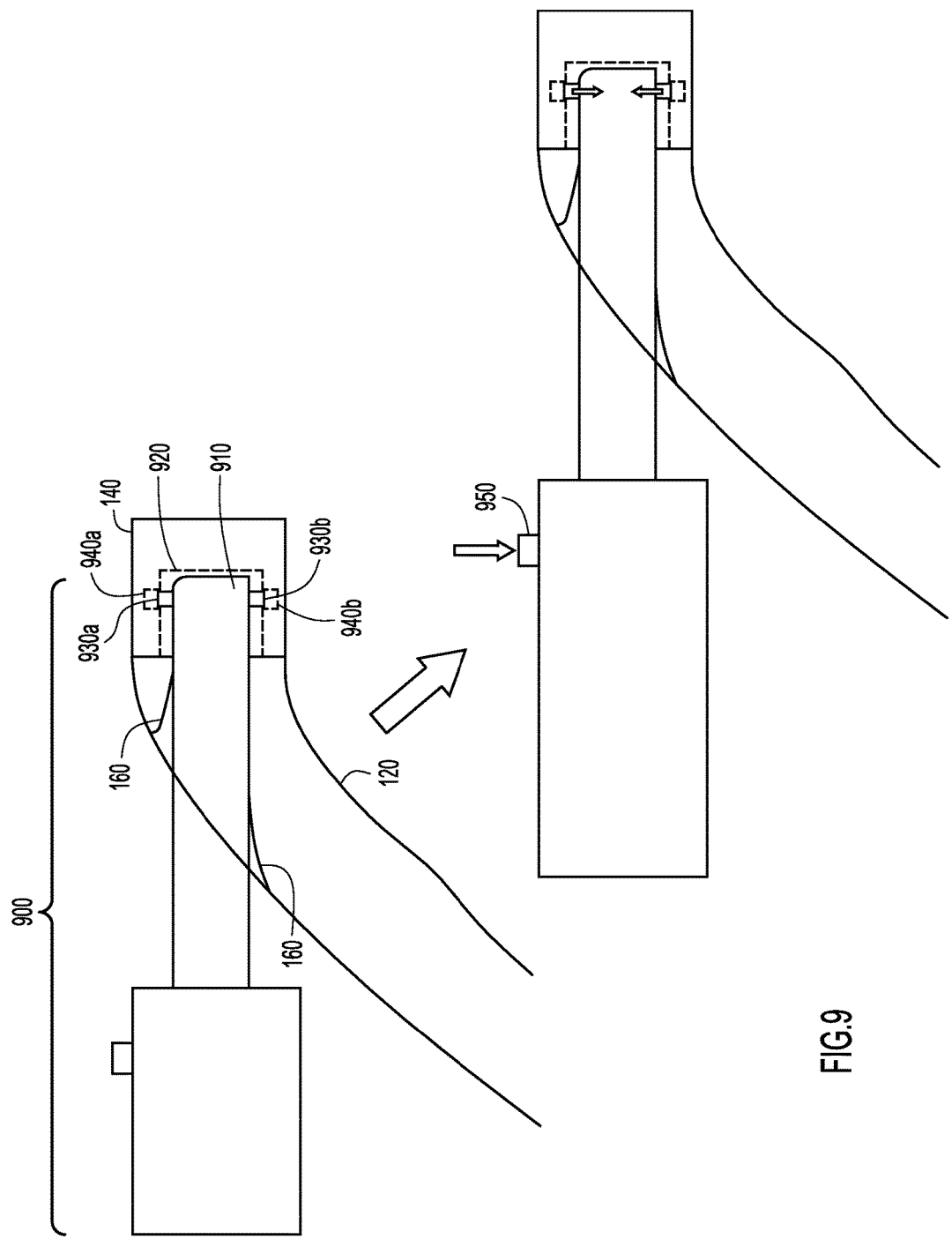
FIG. 9 illustrates an insertion tool and process for placing a lacrimal stent, according to an example embodiment.

With reference now made to FIG. 9, depicted therein is a tool 900 that may be used to facilitate the insertion of first distal end 120 into a punctum, through a canaliculus, and into a lacrimal sac. Specifically, tool 900 is inserted through one-way valve 160 in distal end 120. One-way valve 160 permits insertion tool 900 to enter elongated body 110 while preventing fluid flow out of elongated body 110 when tool 900 is not inserted into elongated body 900.

Once inserted through one-way valve 160, male portion 910 of insertion tool 900 engages female portion 920 formed in first magnet 140. Once male portion 910 is engaged with female portion 920, pins 930a and 930b may engage with second female portions 940a and 940b to secure male portion 910 in female portion 920. Once secured in female portion 920, insertion tool 900 may be used to insert first distal end 120 and first magnet 140 into a punctum, through a canaliculus, and into a lacrimal sac. Though not illustrated, a second distal end and magnetic material of a stent may be constructed in an analogous manner so that a second insertion tool may be used to insert the second distal end into a punctum, through a canaliculus, and into the lacrimal sac.

Once first distal end is inserted into the lacrimal sac, a user may depress button 950. The depression of button 950 retracts pins 930a and 930b, which allows male portion 910 to be disengaged from female portion 920, and insertion tool 900 to be removed from elongated body 110 via one-way valve 160.

Through the use of the devices and techniques described herein, lacrimal stent may be placed in an office or an outpatient setting with or without local anesthesia. A lacrimal stent according to the devices and techniques described herein is easy to place, and once placed in a lacrimal sac the stent cannot be dislodged and remains securely in place.

The above description is intended by way of example only. Although the techniques are illustrated and described herein as embodied in one or more specific examples, it is nevertheless not intended to be limited to the details shown, since various modifications and structural changes may be made within the scope and range of equivalents of the claims.

What is claimed is:
1. An apparatus comprising:
   a flexible tube comprising a first distal end, a second distal end, and an elongated body between the first distal end and the second distal end;

a first magnet arranged at the first distal end of the flexible tube; and
a magnetic material arranged at the second distal end of the flexible tube,
wherein the flexible tube flexes so that the first magnet of the first distal end magnetically engages the magnetic material of the second distal end when the first distal end is inserted into a lacrimal sac of an eye through a first punctum and the second distal end is inserted into the lacrimal sac of the eye through a second punctum, and
wherein the first magnet and the magnetic material are configured to maintain engagement of the first distal end to the second distal end when the first distal end and the second distal end are rotated out of the lacrimal sac.

2. The apparatus of claim 1, wherein the magnetic material comprises a second magnet.

3. The apparatus of claim 2, wherein
the first magnet comprises a first north pole and a first south pole, wherein the first north pole is axially aligned with the flexible tube, where the first north pole is distal from the first distal end of the flexible tube, and wherein the first south pole is proximate the first distal end of the flexible tube, and
the second magnet comprises a second north pole and a second south pole, wherein the second south pole is axially aligned with the flexible tube, wherein the second south pole is distal from the second distal end of the flexible tube, and wherein the second north pole is proximate the second distal end of the flexible tube, and
the first north pole of the first magnet magnetically engages the second south pole of the second magnet when the first distal end is inserted into the lacrimal sac of the eye and the second distal end is inserted into the lacrimal sac of the eye.

4. The apparatus of claim 1, wherein the flexible tube further comprises an opening from an interior of the elongated body to an exterior of the elongated body.

5. The apparatus of claim 1, wherein the first magnet and the magnetic material are configured to secure the first distal end to the second distal end as the flexible tube is rotated through the first punctum and the second punctum such that the first distal end and the second distal end rotate out of the lacrimal sac.

6. The apparatus of claim 5, wherein the first magnet and the magnetic material are removable from the elongated tube after the first distal end and the second distal end rotate out of the lacrimal sac.

7. An ophthalmic surgical kit, comprising:
a flexible tube comprising a first distal end, a second distal end, and an elongated body between the first distal end and the second distal end;
a first magnet arranged at the first distal end of the flexible tube;
a magnetic material arranged at the second distal end of the flexible tube, and a sleeve,
wherein the flexible tube flexes so that the first magnet of the first distal end magnetically engages the magnetic material of the second distal end when the first distal end is inserted into a lacrimal sac of an eye through a first punctum and the second distal end is inserted into the lacrimal sac of the eye through a second punctum,
wherein the first magnet and the magnetic material are configured to secure the first distal end to the second distal end as the flexible tube is rotated through the first punctum and the second punctum such that the first distal end and the second distal end rotate out of the lacrimal sac;
wherein the first magnet and the magnetic material are removable from the elongated tube after the first distal end and the second distal end rotate out of the lacrimal sac, and
wherein the sleeve connects the first distal end with the second distal end after the first magnet and the magnetic material are removed from the elongated tube.

8. The ophthalmic surgical kit of claim 7, further comprising medicine arranged within at least one of the sleeve or the flexible tube.

9. The ophthalmic surgical kit of claim 7, wherein the sleeve secures the first distal end and the second distal end as the flexible tube is rotated so that the first distal end and the second distal end rotate into the lacrimal sac through one of the first punctum or the second punctum and so that the sleeve is arranged within the lacrimal sac.

10. The apparatus of claim 1, wherein;
the first magnet comprises a first female portion arranged at a proximal end of the first magnet and configured to receive a first male portion of a first insertion device;
the magnetic material comprises a second female portion arranged at a proximal end of the magnetic material and configured to receive a second male portion of a second insertion device,
the first distal end comprises a first one-way valve to allow insertion of the first male portion of the first insertion device into the first female portion; and
the second distal end comprises a second one-way valve to allow insertion of the second male portion of the second insertion device into the second female portion.

11. A method comprising:
inserting a flexible tube into a lacrimal sac of an eye, wherein the flexible tube comprises:
a first distal end,
a second distal end,
an elongated body between the first distal end and the second distal end,
a first magnet arranged at the first distal end of the flexible tube, and
a magnetic material arranged at the second distal end of the flexible tube, and wherein inserting the flexible tube into the lacrimal sac comprises:
inserting the first distal end of the flexible tube into a first punctum,
inserting the second distal end into a second punctum, and
positioning the first distal end and the second distal end into the lacrimal sac of the eye such that the flexible tube flexes so that the first magnet of the first distal end magnetically engages the magnetic material of the second distal end while the first distal end and the second distal end are arranged within the lacrimal sac.

12. The method of claim 11, further comprising rotating the flexible tube while the first magnet is magnetically engaged with the magnetic material so that the first distal end and the second distal end exit one of the first punctum or the second punctum.

13. The method of claim 12, further comprising:
removing the first magnet from the first distal end;
removing the magnetic material from the second distal end; and
applying a sleeve to the first distal end and the second distal end.

14. The method of claim 13, further comprising releasing medicine contained in at least one of the sleeve or the elongated body onto a surface of the eye through an opening in the elongated body.

15. The method of claim 13, wherein
removing the first magnet from the first distal end comprises trimming the first distal end; and
removing the magnetic material from the second distal end comprises trimming the second distal end.

16. The method of claim 13, further comprising rotating the flexible tube so that the first distal end and the second distal end rotate into the lacrimal sac through one of the first punctum or the second punctum, and so that the sleeve sits within the lacrimal sac.

17. The method of claim 11, wherein inserting the flexible tube into the lacrimal sac of the eye further comprises:
engaging a first male portion of an first insertion tool with a female portion of the first magnet; and
engaging a second male portion of a second insertion tool with a second female portion of the magnetic material.

18. The method of claim 17, wherein inserting the flexible tube into the lacrimal sac of the eye further comprises:
pushing, via the first insertion tool, the first distal end through the first punctum, through a first canaliculus, into the lacrimal sac, and
pushing, via the second insertion tool, the second distal end through the second punctum, through a second canaliculus, into the lacrimal sac.

19. The method of claim 11, positioning the first distal end and the second distal end into the lacrimal sac of the eye comprises positioning the first distal end and the second distal end such that a magnetic force between the first magnet and the magnetic material pulls the first magnet into magnetic engagement with the magnetic material.

20. The method of claim 19, wherein the magnetic material comprises a second magnet.

* * * * *